(12) United States Patent
Gries et al.

(10) Patent No.: US 11,274,110 B2
(45) Date of Patent: Mar. 15, 2022

(54) PROCESS FOR PREPARING BENZOTHIOPHEN-2YL BORONATE

(71) Applicant: Bayer Pharma Aktiengesellschaft, Berlin (DE)

(72) Inventors: Jörg Gries, Haan (DE); Johannes Platzek, Berlin (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 16/759,139

(22) PCT Filed: Oct. 18, 2018

(86) PCT No.: PCT/EP2018/078586
§ 371 (c)(1),
(2) Date: Apr. 24, 2020

(87) PCT Pub. No.: WO2019/081346
PCT Pub. Date: May 2, 2019

(65) Prior Publication Data
US 2020/0339606 A1 Oct. 29, 2020

(30) Foreign Application Priority Data
Oct. 25, 2017 (EP) ..................................... 17198336

(51) Int. Cl.
*C07D 333/54* (2006.01)
*C07F 5/02* (2006.01)
*C07D 333/72* (2006.01)
*C07D 487/04* (2006.01)

(52) U.S. Cl.
CPC ............ *C07F 5/025* (2013.01); *C07D 333/54* (2013.01); *C07D 333/72* (2013.01); *C07D 487/04* (2013.01)

(58) Field of Classification Search
CPC ..... C07F 5/025; C07D 333/54; C07D 333/72; C07D 487/04
USPC ........................................................ 514/183
See application file for complete search history.

(56) References Cited

U.S. PATENT DOCUMENTS 9,206,184 B2   12/2015   Brohm et al.
2014/0336173 A1  11/2014   Brohm et al.
2019/0016724 A1   1/2019   Brohm et al.

FOREIGN PATENT DOCUMENTS

WO   2013087578 A1   6/2013

OTHER PUBLICATIONS

Ellanova Laboratories LC (Aug. 8, 2012). "Benzo[b]thiophene,5-(chloromethyl)-7-methoxy-", Chemical Catalog, pp. 1-1, XP055523647, abstract.
International Search Report dated Jan. 21, 20219 for PCT Application No. PCT/EP2018/078586, filed Oct. 18, 2018, 2 pages.
U.S. Appl. No. 14/365,424, filed Jun. 13, 2014, for Dirk Brohm et al. (Also published as US 2014-0336173 cited herewith) (U.S. Patent Application is not submitted herewith pursuant to the waiver of 37 C.F.R. § 1.98(a)(2)(iii) issued by the Office on Sep. 21, 2004.).
U.S. Appl. No. 15/900,725, filed Feb. 20, 2018, for Dirk Brohm et al. (Also published as US 2019-0016724, cited herewith) (U.S. Patent Application is not submitted herewith pursuant to the waiver of 37 C.F.R. § 1.98(a)(2)(iii) issued by the Office on Sep. 21, 2004.).
U.S. Appl. No. 17/310,347, filed Jul. 28, 2021, for Jörg Gries et al. (U.S. Patent Application is not submitted herewith pursuant to the waiver of 37 C.F.R. § 1.98(a)(2)(iii) issued by the Office on Sep. 21, 2004.).

*Primary Examiner* — Kahsay Habte
(74) *Attorney, Agent, or Firm* — Morrison & Foerster LLP

(57) ABSTRACT

A process for preparing the benzothiophen-2-yl boronate of formula (VI) which serves as an intermediate for production of medicaments and for production of medicaments for treatment and/or prophylaxis of proliferative disorders, such as cancer and tumor diseases.

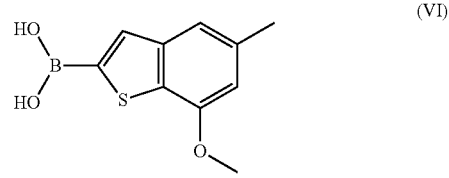

(VI)

34 Claims, No Drawings

PROCESS FOR PREPARING BENZOTHIOPHEN-2YL BORONATE

CROSS REFERENCE TO RELATED APPLICATIONS

This application is a national stage application under 35 U.S.C. § 371 of International Application No. PCT/EP2018/078586, filed internationally on Oct. 18, 2018, which claims the benefit of priority to European Application No. 17198336.4, filed Oct. 25, 2017.

FIELD OF THE INVENTION

The present application relates to a novel and efficient process for preparing benzothiophen-2-yl boronate of formula (VI)

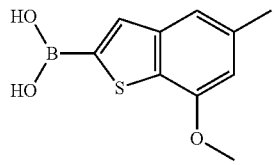

which serves as an intermediate for production of medicaments and for production of medicaments for treatment and/or prophylaxis of proliferative disorders, such as cancer and tumor diseases.

BACKGROUND OF THE INVENTION

More particularly, the benzothiophen-2-yl boronates of the formula (VI) are suitable for the preparation of compounds of the formula (I)

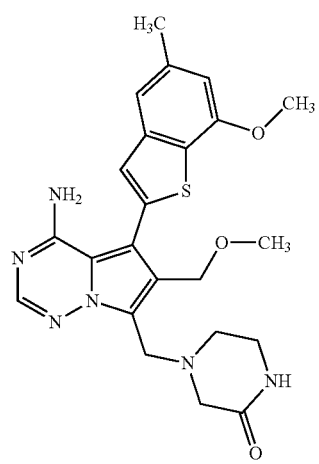

4-{[4-Amino-6-(methoxymethyl)-5-(7-methoxy-5-methyl-1-benzothiophen-2-yl)pyrrolo[2,1 f]¬[1,2,4]¬triazin-7-yl]methyl}piperazin-2-one or a pharmaceutically acceptable salt, hydrate, or solvate thereof, which serves for production of medicaments and for production of medicaments for treatment and/or prophylaxis of proliferative disorders, such as cancer and tumor diseases.

4-{[4-Amino-6-(methoxymethyl)-5-(7-methoxy-5-methyl-1-benzothiophen-2-yl)pyrrolo[2,1 f]¬[1,2,4]¬triazin-7-yl]methyl}piperazin-2-one has been given the INN ROGARATINIB.

Rogaratinib has valuable pharmacological properties and can be used for the prevention and treatment of disorders in humans and other mammals.

Rogaratinib is a potent inhibitor of the activity or expression of receptor tyrosine kinases, particularly of the FGFR kinases, and most notably of the FGFR-1 and FGFR-3 kinases. In certain embodiments, the disorders relating to the activity of FGFR kinases are proliferative disorders, in particular cancer and tumor diseases.

Cancer is a leading cause of death worldwide and accounted for 7.6 million deaths (around 13% of all deaths) in 2008. Deaths from cancer are projected to continue to rise worldwide to over 11 million in 2030 (WHO source, Fact Sheet No. 297, February 2011).

A process for preparation of Rogaratinib as well as the synthesis of the key intermediate the benzothiophen 2-yl boronates is disclosed in WO 2013/087578.

The benzothiophen-2-yl boronates of formula (VI) can conveniently be prepared starting from the substituted thiophenol derivatives of formula (XXIV) (see Scheme 1 below).

Alkylation with bromo-acetal (XXV) and subsequent polyphosphoric acid-mediated cyclization provides the benzothiophene intermediates of formula (XXVII) which are then metalated in 2-position and reacted with a trialkyl borate. Alkaline work-up affords the free (benzothiophen-2-yl)boronic acids of formula (VIa) which may be transformed, if desired, into cyclic boronates, e.g. so-called MIDA boronates of formula (VIb), by standard procedures known in the art [see, for example, D. M. Knapp et al., *J Am. Chem. Soc.* 131 (20), 6961-6963 (2009)].

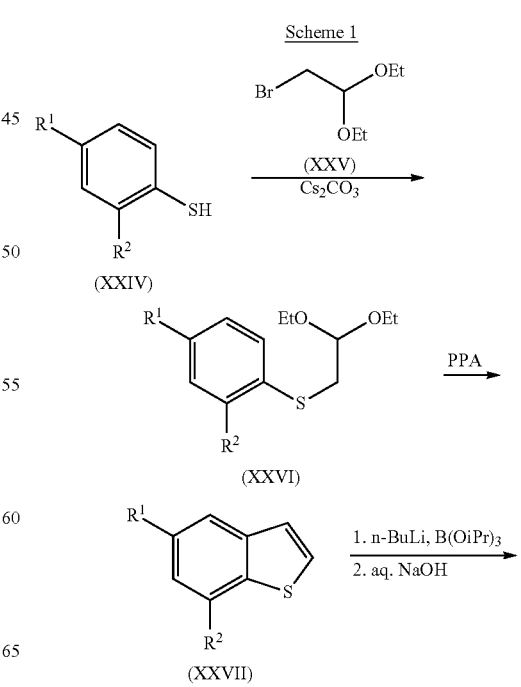

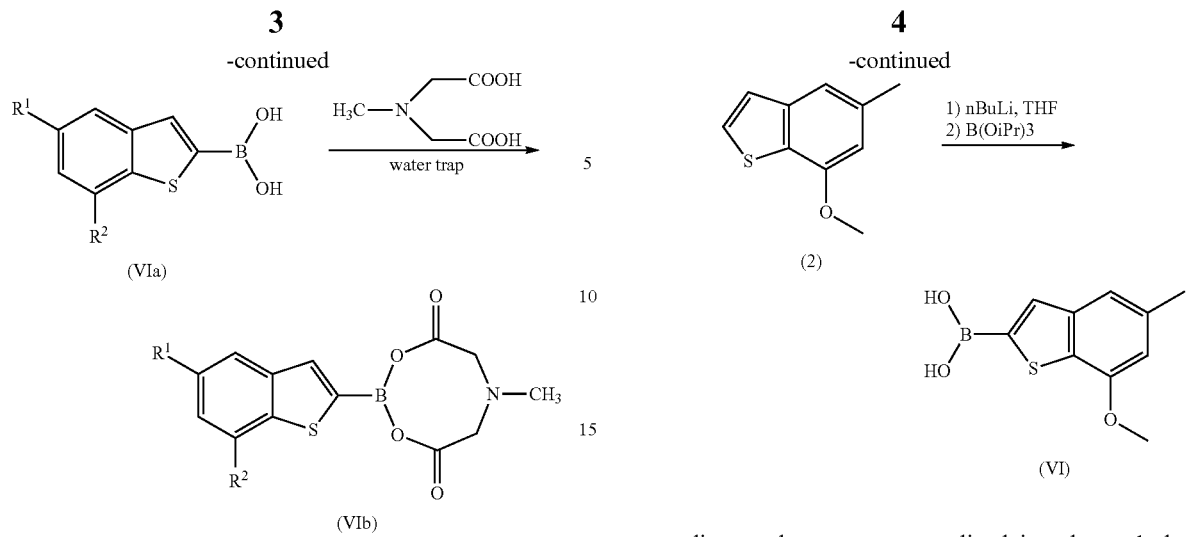

[cf P. A. Plé and L. J. Marnett, *J. Heterocyclic Chem.* 25 (4), 1271-1272 (1988); A. Venturelli et al., *J. Med. Chem.* 50 (23), 5644-5654 (2007)].

The compounds of the formula (XXIV) are either commercially available, known from the literature, or can be prepared from readily available starting materials by adaptation of standard methods described in the literature. Detailed procedures and literature references for preparing the starting materials can also be found in the Experimental Part in the section on the preparation of the starting materials and intermediates of WO 2013/087578.

- The synthesis according to the above shown scheme has the general disadvantage that the ring-closure leading to compounds of the formula (XXVII) needs harsh conditions, such as unusually high reaction temperatures and unfavourable reagents, such as syrup-like polyphosphoric acid which can form biphasic systems with the reaction mixture. These conditions necessitate considerable safety precautions and substantial engineering effort on conversion to the industrial scale and thus causes high production costs.
- The synthesis according to the above shown scheme has the disadvantage of formation of impurities of high structural similarity due to mentioned drastic reaction conditions, which only can be purged by extensive purification efforts on compounds of the formula (XXVII) or at following stages of the synthesis. This leads to additional effort, cost and significant reduction of yield—especially on industrial scale. These impurities even may not be purged to the extent that is needed for pharmaceutical products according to the appropriate regulatory guidelines.

During the preparation of the benzothiophen-2-yl boronates of the formula (VI) via ring closure of (1) to (2):

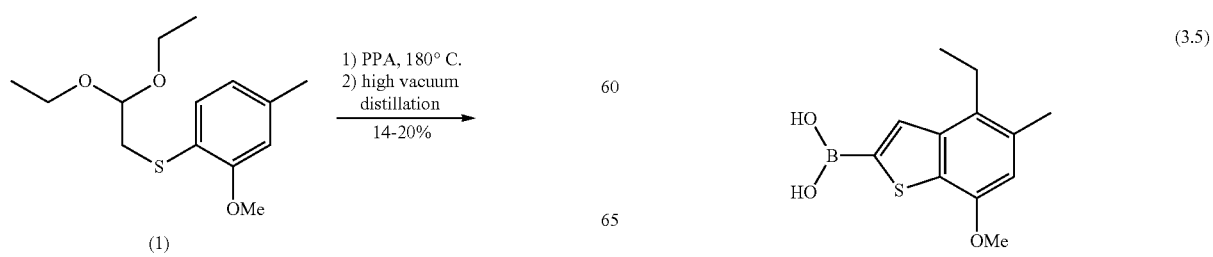

according to the process as outlined in scheme 1 the formation of impurities was observed that comply with structures of the formulas 3.1 to 3.6 according to mass spectroscopy.

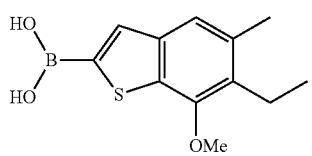
(3.6)

These impurities could be traced back to impurities that comply with structures of the formulas 4.1 to 4.6 in the methoxy-methyl-benzothiophene intermediate (2).

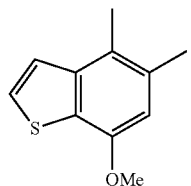
(4.1)

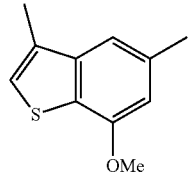
(4.2)

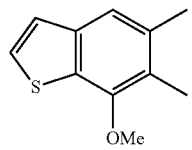
(4.3)

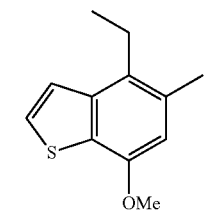
(4.4)

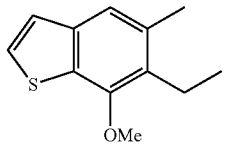
(4.5)

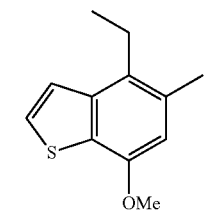
(4.6)

These impurities are formed during the ring-closure process with PPA at high temperatures and were purged by fractionated high vacuum distillation of (2), which reduces the yield to 14-20% on industrial scale, but still not leads to impurity levels that match the requirements for APIs in late stage clinical development.

It is an object of the present invention to provide an efficient process with high yield for preparation of benzothiophen-2-yl boronates of the formula (VI)

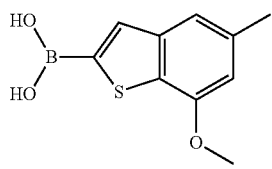
(VI)

as a key component for an efficient process with high yield for preparation of compound of the formula (I)

(I)

[structure of compound I]

or a pharmaceutically acceptable salt, hydrate, or solvate thereof.

SUMMARY OF THE INVENTION

The present invention relates to a method of preparing a compound of formula (VI):

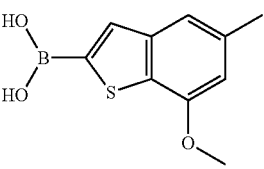
(VI)

comprising the following steps:
step 5:
wherein a compound of formula (VII):

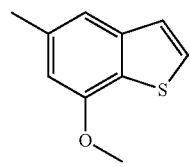
(VII)

is allowed to react, by dissolution of compound of formula (VII) in an inert solvent such as THF, and addition of a metal organic base such as a n-butyl lithium solution and a trialkyl borate such as tri iso-propyl borate, optionally in a solvent, such as THF, thereby providing a compound of formula (VI):

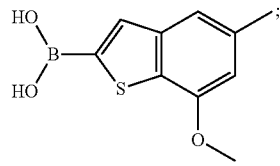
(VI)

said compound of formula (VII):

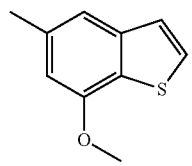
(VII)

being prepared by the following step 4:
wherein a compound of formula (X):

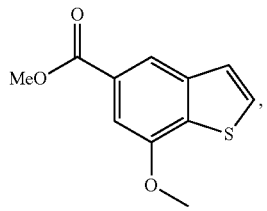
(X)

is allowed to react, optionally in the presence of an inert solvent, such as THF for example, with one or more reducing agents, such as a sodium-bis(2-methoxy-ethoxy)-aluminium-dihydride solution for example, thereby providing a compound of formula (IX):

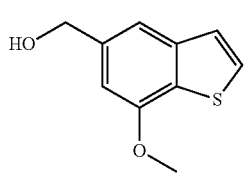
(IX)

and allowing the compound of formula (IX) to react with aqueous HCl in the presence of a solvent such as toluene for example, thereby providing a compound of formula (VIII):

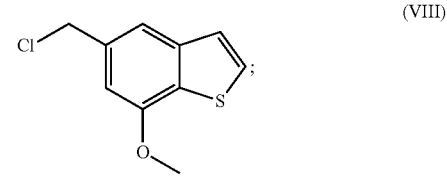
(VIII)

and allowing the compound of formula (VIII) to react with one or more reducing agents, such as a sodium-bis(2-methoxy-ethoxy)-aluminium-dihydride solution for example, thereby providing a compound of formula (VII).

The present invention also relates to a compound selected from:

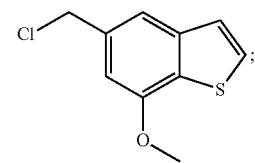
(VIII)

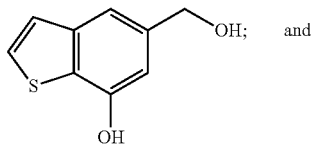
(XVI)

and

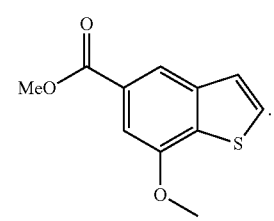
(X)

DETAILED DESCRIPTION OF THE INVENTION

As stated above, it is an object of the present invention to provide an efficient process with high yield for preparation of benzothiophen-2-yl boronates of the formula (VI)

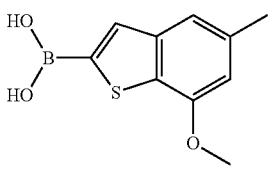
(VI)

as a key component for an efficient process with high yield for preparation of compound of the formula (I)

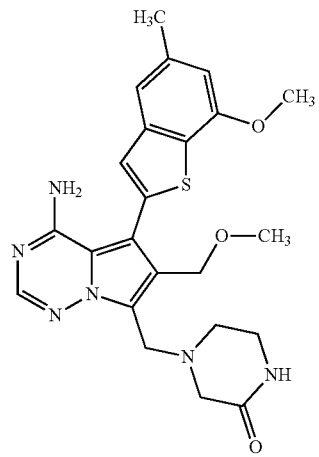
(I)

or a pharmaceutically acceptable salt, hydrate, or solvate thereof.

This object is achieved in accordance with the present invention, as follows. Scheme 2 below illustrates the individual reaction steps by way of example.

Scheme 2

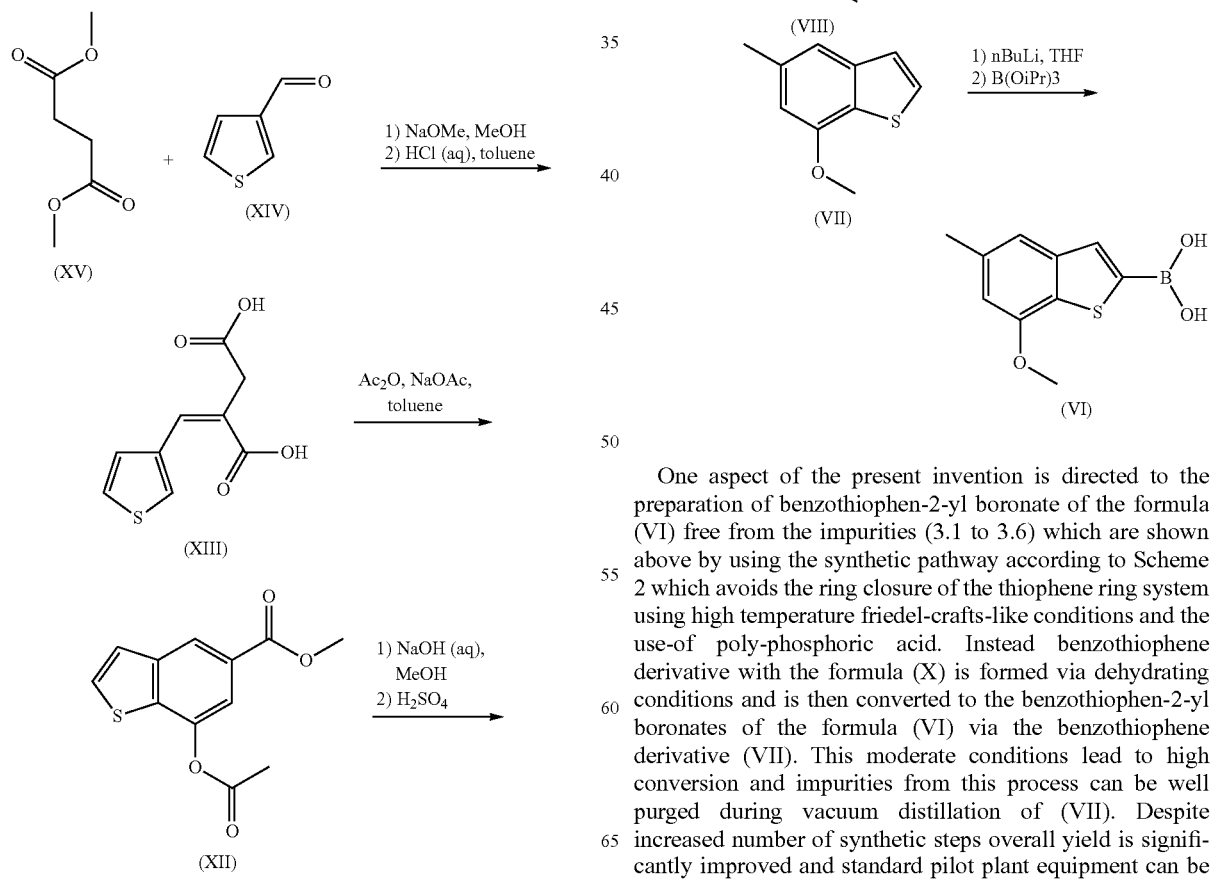

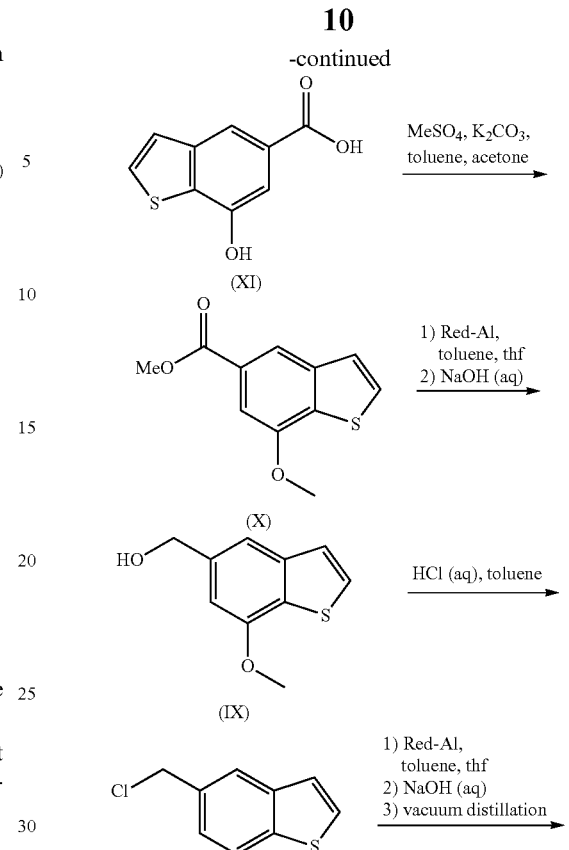

One aspect of the present invention is directed to the preparation of benzothiophen-2-yl boronate of the formula (VI) free from the impurities (3.1 to 3.6) which are shown above by using the synthetic pathway according to Scheme 2 which avoids the ring closure of the thiophene ring system using high temperature friedel-crafts-like conditions and the use-of poly-phosphoric acid. Instead benzothiophene derivative with the formula (X) is formed via dehydrating conditions and is then converted to the benzothiophen-2-yl boronates of the formula (VI) via the benzothiophene derivative (VII). This moderate conditions lead to high conversion and impurities from this process can be well purged during vacuum distillation of (VII). Despite increased number of synthetic steps overall yield is significantly improved and standard pilot plant equipment can be used, leading to significant reduction of production cost.

The ring closure disclosed in steps 1 and 2 below are already known in a modified form from EP 2338887 A1 Reference Examples 12 and 13, as well as a further modified version from JACS Vol 129, No. 45, 2007 Boger et al.

The following disadvantages are connected with this lab scale processes leading to ethyl 7-acetoxy-3-methylbenzo [b]thiophene-5-carboxylate according to Boger, et al.: Low overall yields are observed—probably due to decomposition of the thiophen-aldehyde under basic reaction conditions during the condensation reaction. Therefore high amounts of succinate reagents were applied (e.g. 6 equivalents). In the ring closure reaction under dehydrating conditions a large access of acetic acid anhydride was applied by using acetic acid anhydride as a solvent at high reaction temperatures of up to 140° C. As a result the product Ethyl 7-Acetoxy-3-methylbenzo[b]thiophene-5-carboxylate could only be isolated in 40% yield after purification by chromatography. Furthermore a reaction in refluxing acetic acid anhydride would need significant safety and engineering considerations during scale-up.

We unexpectedly could achieve high conversion in the condensation reaction towards intermediate (XIII) by changing the order of addition through adding the thiophene-3-aldehyde to a mixture of succinic ester and sodium methanolate. Under these conditions only a slight excess of succinate (2.5. equivalents) has to be applied. Side components and excess reagents can be purged at this early stage by crystallization of this intermediate e.g. from toluene, avoiding chromatographic purification on a later stage.

Furthermore the ring closure under dehydrating conditions could be completed with a low excess of acetic acid anhydride diluted by toluene as an inert solvent at moderate temperatures of only 75° C. within 7 hours. These conditions facilitate less side reactions and safe work-up of the reaction mass on industrial scale. If the crude intermediate benzothiophene carboxylic ester (XII) is then subjected to saponification with aqueous NaOH in MeOH, followed by neutralization with an acid, the benzothiophene carboxylic acid can be isolated in high yield and purity as a solid.

A first aspect of the present invention is directed to a process for the preparation of benzothiophen-2-yl boronates of formula (VI).

Step 1:

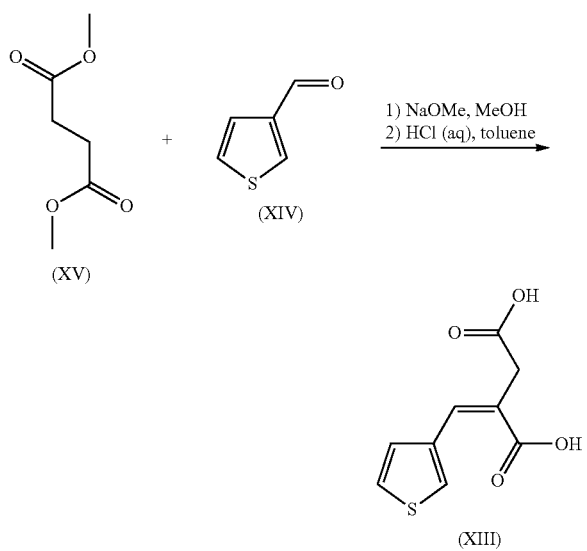

According to the first aspect of the present invention the reaction of (XV) and (XIV) to (XIII) as shown above is carried out by condensation of (XV) with (XIV). This is done by adding a solution of an alkali alcoholate, such as sodium methanolate, in an alcohol, preferably methanol to a solution of dimethyl succinate at 25-40° C. Other succinate esters can be used in place of (XV), as the esters are cleaved during following steps.

The mixture is heated to reflux and a solution of thiophene-3-aldehyde is added. After complete conversion the mixture is hydrolyzed by addition of water and the product is extracted with toluene. (or other non-water miscible solvents) After removal of the solvent the crude (XIII) is purified by crystallization and/or reslurry from toluene (or other suitable solvents).

This process has the advantage of high conversion related to the aldehyde by slow addition of the thiophene-3-aldehyd to the reaction mixture.

This process has the advantage of applying reduced excess of dimethyl succinate for full conversion.

This process has the advantage of giving a very pure and solid intermediate (XIII) after purification by crystallization or/reslurry, contributing to avoidance of purification on later stages by e.g. preparative chromatography.

Step 2:

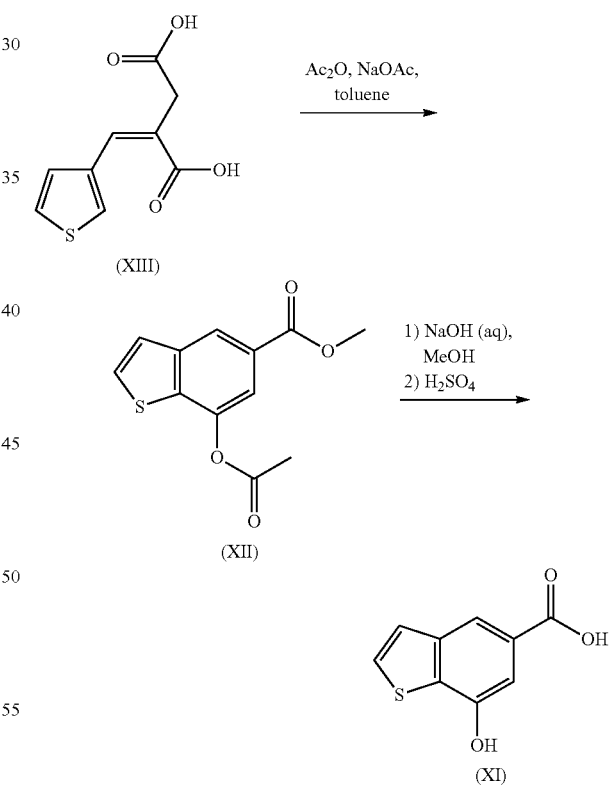

According to the first aspect of the invention, the reaction of (XIII) to the carboxylic acid intermediate (XI) via (XII) as shown in Step 2 is carried out by ring-closure to the benzothiophen derivative (XII) under dehydrating conditions and hydrolysis of the ester moieties yielding the 7-hydroxy-1-benzothiophene-5-carboxylic acid (XI). This is done by heating (XIII) with acetic acid anhydride and sodium acetate in toluene at 70-75° C. for 7 h (other dehydrating agents: e.g. acid anhydrides (trifluoracetic acid anhydride), methyl chloro formate; other bases than sodium acetate (potassium acetate; T & t can be varied for all process steps). The mixture is hydrolyzed by addition of water at 25-30° C. The organic phase is separated, washed with water, again, and the solvent is partially removed by distillation under reduced pressure. The remaining solution of (XII) in toluene is diluted with MeOH and water and an aqueous sodium hydroxide solution (other bases, mainly inorganic) is slowly added at temperatures below 45° C. and finally heated to 50-55° C. for 5 h. The aqueous phase is separated and further diluted with water and the product is precipitated by addition of a strong protic acid such as HCl, $HNO_3$, sulfonic acids, $CH_3COOH$ and $H_2SO_4$, preferably $H_2SO_4$ at 10-15° C. till a pH of 2-3 is reached. The suspension is heated to 40-45° C. and cooled to 25-30° C. within 2 h to improve filtration behavior of the product, and isolated by filtration.

- This process has the advantage of increased process safety for industrial scale by not using a large excess of acetic acid anhydride as a solvent, but a limited excess by dilution in toluene. Safe work-up is achieved by controlled release of energy during hydrolyzation of acetic acid anhydride under diluted conditions.
- This process has the advantage of giving reduced amounts of side products by using only moderate reaction temperatures during the ring closure step towards (XII).
- This process has the advantage of acceptable filtration times on industrial scale during isolation of (XI) by improving solid state properties during temperature treatment before isolation.
- This process has the advantage of yielding a well crystalizing solid product of intermediate (XI) with very high purity in very good yield, avoiding additional purification steps on intermediate (XII) or later stages of the synthesis.

Step 3:

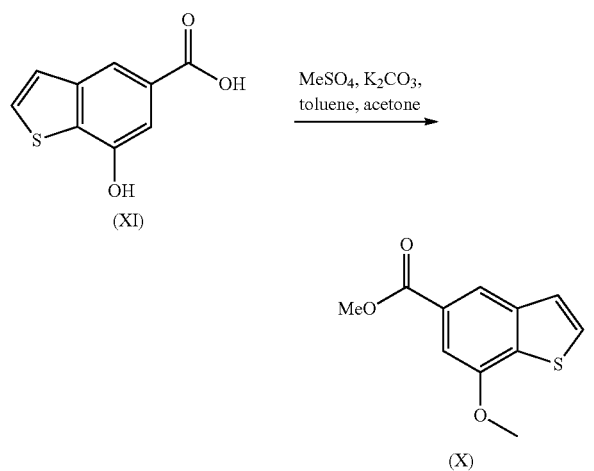

According to the first aspect of the present invention, the reaction of (XI) to methyl 7-methoxy-1-benzothiophene-5-carboxylate (X) as shown in scheme is carried out by methylating the ester and phenol moiety. This is done by dissolving (XI) in a mixture of acetone and toluene (other solvents). After addition of a potassium carbonate (other bases inorganic, amines . . . ) the suspension is heated to 50-60° C. and dimethylsulfate (other methylating agents: methyl iodide) is slowly added. After full conversion the solvent is partially distilled of at 85° C. and water is added. Phases are separated and aqueous phase is additionally extracted with toluene. Combined organic phases are washed with water and the solvent is removed under reduced pressure at 60° C. The crude product is submitted to the next step.

Step 4:

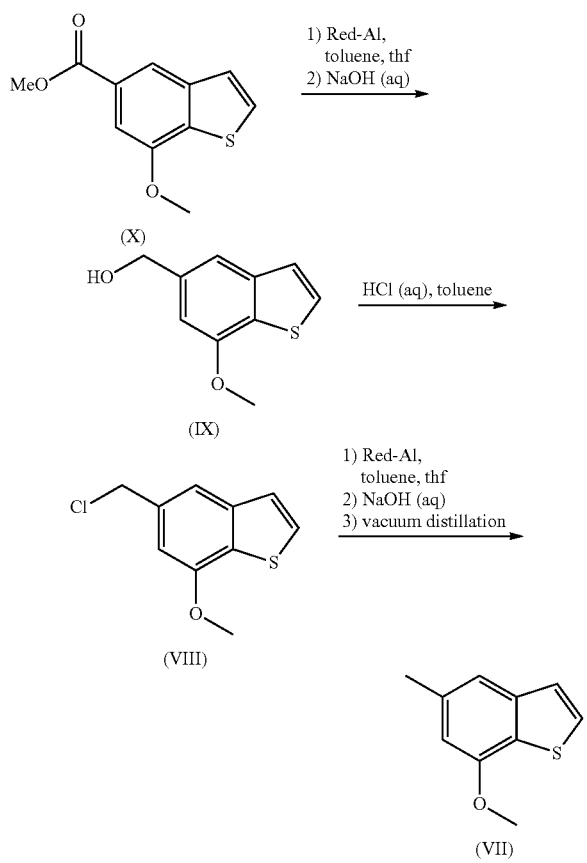

According to the first aspect of the present invention, the reaction of (X) to 7-methoxy-5-methyl-1-benzothiophene (VII) is done by reduction of the ester moiety to the methyl group yielding (VII). This is preferentially achieved by stepwise reduction through reducing the ester moiety of (X) to the alcohol (IX), followed by chlorination of the alcohol moiety to (VIII), followed by reduction to (VII) as shown in Step 4. This is done by dissolving the crude product (X) in an inert solvent such as ethers, for example dioxane Me-THF, CPME, and MTBE, aromatic & aliphatic hydrocarbons, for example benzene, toluene, xylol cyclohexane; preferably THF is used and addition of sodium-bis(2-methoxy-ethoxy)-aluminium-dihydride (Red-Al®) solution in toluene at 25-30° C. Other suitable reducing agents include hydrogen (with a suitable catalyst), LAH, boranes and silanes.

The mixture is hydrolyzed by addition of aqueous sodium hydroxide solution (other aqueous bases) and the product is extracted with toluene (other no-water miscible solvents or precipitated/crystallized by anti-solvent addition) and isolated by removing the solvent under reduced pressure at 60° C.

Crude (IX) is dissolved in toluene and at 50-55° C. aqueous HCl is slowly added. Other chlorinated agents such as SOCl₂ may be utilized. After complete conversion the mixture is hydrolyzed with aqueous sodium bicarbonate solution. The organic phase is dried by treatment with brine, Na₂SO₄ and azeotropic drying by removing the solvent under reduced pressure at 60° C.

Also, other leaving groups can be used as an alternative chlorine in structure (VIII), such as Br, I, F, RSO₃, for example.

Crude product (VIII) is dissolved in an inert solvent such as ethers, for example Dioxane Me-THF, CPME, and MTBE, aromatic & aliphatic hydrocarbons, for example benzene, toluene, xylol cyclohexane; preferably THF is used and a reduced using a reducing agent such as sodium-bis (2-methoxy-ethoxy)-aluminum-dihydride (Red-Al®) solution in toluene is added at 25-30° C. Other suitable reducing agents include hydrogen (with a suitable catalyst), LAH, boranes and silanes.

The mixture is hydrolyzed by addition of aqueous sodium hydroxide solution (other aqueous bases) and the product is extracted with toluene (other no-water miscible solvents or precipitated/crystallized by anti-solvent addition) and isolated by removing the solvent under reduced pressure at 60° C. (VIII) is purified by distillation under vacuum at 125-160° C.

This process has the advantage of giving 7-methoxy-5-methyl-1-benzothiophene (VII) in high yield and high purity without impurities according to Scheme 1 which are critical in regard of the quality of the final pharmaceutical ingredient (I) for clinical applications and cannot be easily purged in one of the following process steps towards (I).

This process has the advantage of giving 7-methoxy-5-methyl-1-benzothiophene (VII), using standard multi-purpose equipment and safe reagents on industrial scale. The use of drastic reaction conditions like high temperatures >160° C. and unfavourable reagents like syrup-like polyphosphoric acid, which is not completely dissolved in the reaction mixture, is avoided. Very costly safety and engineering considerations on industrial scale are therefore avoided.

Step 5:

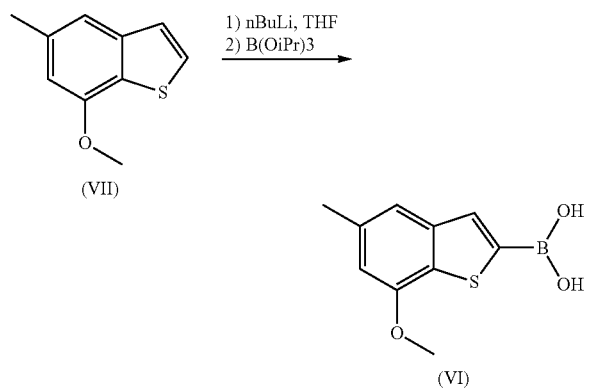

According to the first aspect of the present invention, the reaction of (VII) to benzothiophen-2-yl boronates of the formula (VI) is done by borylation. (VII) is dissolved in an inert solvent such as THF and metallated by addition to a metal organic base such as n-butyl lithium solution in THF/hexane at −73 to −80° C. After stirring the reaction mass for 30 minutes triisopropyl borate is slowly added at −73 to −80° C. After a reaction time of 30 minutes, the mixture is hydrolyzed with aqueous potassium hydroxide solution at <10° C. and phases are separated at 20-30° C. Aqueous phase is washed with toluene and product is precipitated by addition of aqueous sulfuric acid solution at 0-5° C. (other acids). (VI) is isolated by filtration and washed with water. The product is reslurried with a solvent such as cyclohexane at 40-45° C., isolated and dried at 40-45° C. at reduced pressure.

This process has the advantage of giving (7-methoxy-5-methyl-1-benzothiophen-2-yl) boronic acid (VI) in high yield and high purity without impurities according to Scheme 1 which are critical in regard of the quality of the final pharmaceutical ingredient (I) for clinical applications and cannot be easily purged in one of the following process steps towards (I).

According to an alternate embodiment of the first aspect of the present invention, a route from intermediate (XII) to (X) is shown in the following Scheme 3:

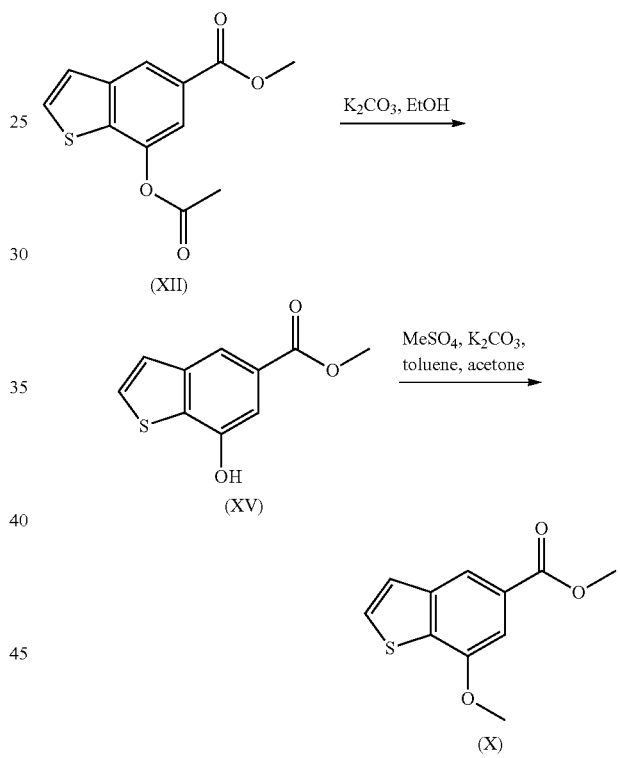

An alternative embodiment of this first aspect of the present invention is the conversion of intermediate (XII) to (X) via intermediate (XV). Only the acetyl function of (XII) is selectively hydrolyzed to the intermediate (XV) by applying a weaker base compared to the process for the preparation of intermediate (XI). This is done by mixing (XII) with potassium carbonate in ethanol at elevated temperature. The reaction mass is hydrolyzed by addition of aqueous hydrogen chloride solution and the product is extracted with methyl t-butyl ether. (XV) is obtained after removal of the solvent at reduced pressure.

The reaction of (XV) to methyl 7-methoxy-1-benzothiophene-5-carboxylate (X) is carried out by treatment with a methylating agent with or without presence of a base. This is done by mixing (XV) with potassium carbonate and dimethyl sulfate in 2-butanone and stirring at room temperature. After complete reaction an aqueous solution of ammonia and methyl t-butyl ether is added. The organic phase is concentrated at reduced pressure yielding (X).

This alternative process has the disadvantage of avoiding a well crystallizing solid product of intermediate (XI). This alternative process has the advantage of allowing telescoping XV as a solution and applying less amount of toxic methylating agent at moderate temperature.

In an alternative embodiment of the first aspect of the present invention, the route from intermediate (XI) to 7-methoxy-5-methyl-1-benzothiophene (VII) is shown in the following Scheme 4:

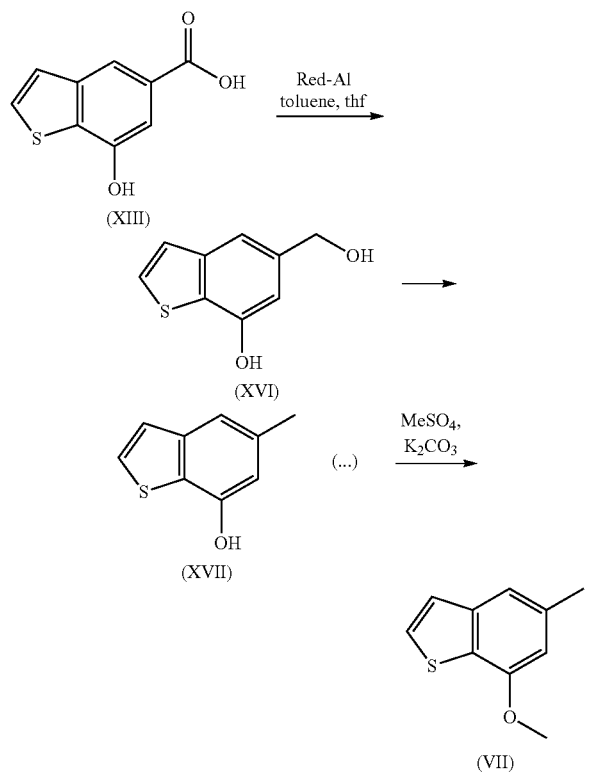

In this route (XIII) is first reduced in a single step giving (XVII) or in 2 steps giving intermediate (XVII) via intermediate (XVI). (XVII) is then methylated to (VII).

Salts for the purposes of the present invention are preferably pharmaceutically acceptable salts of the compounds according to the invention (for example, see S. M. Berge et al., "Pharmaceutical Salts", *J. Pharm. Sci.* 1977, 66, 1-19). Salts which are not themselves suitable for pharmaceutical uses but can be used, for example, for isolation or purification of the compounds according to the invention are also included.

Pharmaceutically acceptable salts include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, formic acid, acetic acid, trifluoroacetic acid, propionic acid, lactic acid, tartaric acid, malic acid, citric acid, fumaric acid, maleic acid, and benzoic acid.

Pharmaceutically acceptable salts also include salts of customary bases, such as for example and preferably alkali metal salts (for example sodium and potassium salts), alkaline earth metal salts (for example calcium and magnesium salts), and ammonium salts derived from ammonia or organic amines, such as illustratively and preferably ethylamine, diethylamine, triethylamine, N,N-diisopropylethylamine, monoethanolamine, diethanolamine, triethanolamine, dimethylaminoethanol, diethylaminoethanol, procaine, dicyclohexylamine, dibenzylamine, N-methylmorpholine, N-methylpiperidine, arginine, lysine, and 1,2-ethylenediamine.

Solvates in the context of the invention are designated as those forms of the compounds according to the invention which form a complex in the solid or liquid state by stoichiometric coordination with solvent molecules. Hydrates are a specific form of solvates, in which the coordination takes place with water. Hydrates are preferred solvates in the context of the present invention.

The compounds of this invention may, either by nature of asymmetric centers or by restricted rotation, be present in the form of isomers (enantiomers, diastereomers). Any isomer may be present in which the asymmetric center is in the (R)-, (S)-, or (R,S)-configuration.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

In addition, all possible tautomeric forms of the compounds described above are included according to the present invention.

The present invention also encompasses all suitable isotopic variants of the compounds according to the invention. An isotopic variant of a compound according to the invention is understood to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, fluorine, chlorine, bromine and iodine, such as $^{2}$H (deuterium), $^{3}$H (tritium), $^{13}$C, $^{14}$C, $^{15}$N, $^{17}$O, $^{18}$O, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body. Due to comparatively easy preparability and detectability, especially compounds labelled with $^{3}$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required. Such modifications of the compounds according to the invention may therefore in some cases also constitute a preferred embodiment of the present invention. Isotopic variants of the compounds according to the invention can be prepared by processes known to those skilled in the art, for example by the methods described below and the methods described in the working examples, by using corresponding isotopic modifications of the particular reagents and/or starting compounds therein.

Unless otherwise noted, suitable bases for the coupling reactions, where necessary, are in particular alkali carbonates, such as sodium, potassium or caesium carbonate, alkali phosphates, such as sodium or potassium phosphate, or alkali fluorides, such as potassium or caesium fluoride. Usually, these bases are employed as aqueous solutions. The reactions are carried out in organic solvents that are inert under the reaction conditions. Preferably, water-miscible organic solvents, such as 1,2-dimethoxyethane, tetrahydrofuran, 1,4-dioxane, acetonitrile, N,N-dimethylformamide (DMF) or dimethylsulfoxide (DMSO), are employed but other inert solvents, such as dichloromethane or toluene, may also be used.

Unless otherwise noted, condensing agents suitable for the process steps, where necessary, include, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide (EDC), phosgene derivatives such as N,N'-carbonyldiimidazole (CDI) or isobutyl chloroformate, α-chloroenamines such as 1-chloro-2-methyl-1-dimethylamino-1-propene, phosphorus compounds such as propanephosphonic anhydride, diethyl cyanophosphonate, bis(2-oxo-3-oxazolidinyl)phosphoryl chloride, benzotriazol-1-yloxy-tris(dimethylamino)-phosphonium hexafluorophosphate (BOP) or benzotriazol-1-yloxy-tris(pyrrolidino)phosphonium hexafluorophosphate (PyBOP), and uronium compounds such as O-(benzo-triazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzo-triazol-1-yl)-1,1,3,3-tetramethyluronium tetrafluoroborate (TCTU), if appropriate in combination with further auxiliaries, such as 1-hydroxybenzotriazole (HOBt) or N-hydroxysuccinimide (HOSu), and/or bases such as alkali carbonates, for example sodium or potassium carbonate, or organic amine bases, such as triethylamine, N-methylpiperidine, N-methylmorpholine (NMM), N,N-diisopropylethylamine (DIPEA), pyridine or 4-N,N-dimethylaminopyridine (DMAP). Preference is given to using O-(7-azabenzotriazol-1-yl)-N,N,N',N'-tetramethyluronium hexafluorophosphate (HATU) or O-(benzotriazol-1-yl)-N,N,N',N'-tetramethyluronium tetrafluoroborate (TBTU) in combination with N,N-diisopropylethylamine (DIPEA) and optionally 1-hydroxybenzotriazole (HOBt).

Unless otherwise noted, acceptable inert solvents for process (where necessary) are, for example, ethers such as diethyl ether, tert-butyl methyl ether, tetrahydrofuran (THF), 1,4-dioxane or 1,2-dimethoxyethane, hydrocarbons such as benzene, toluene, xylene, hexane or cyclohexane, halogenated hydrocarbons such as dichloromethane, trichloromethane, carbon tetrachloride, 1,2-dichloroethane, trichloroethylene or chlorobenzene, or other solvents such as acetone, acetonitrile, ethyl acetate, pyridine, dimethylsulfoxide (DMSO), N,N-dimethylformamide (DMF), N,N'-dimethylpropylene urea (DMPU) or N-methyl-pyrrolidinone (NMP). It is also possible to use mixtures of these solvents. Preference is given to using dichloromethane, tetrahydrofuran, N,N-dimethylformamide or mixtures thereof.

EXAMPLES

Abbreviations and Acronyms

Ac acetyl
$Ac_2O$ acetic anhydride
AcOH acetic acid
aq. aqueous (solution)
Boc tert-butoxycarbonyl
br. broad ($^1$H-NMR signal)
Bu butyl
cat. catalytic
conc. concentrated
d doublet ($^1$H-NMR signal)
DBDMH 1,3-dibromo-5,5-dimethylhydantoin
DCI direct chemical ionization (MS)
DCM dichloromethane
Dess-Martin periodinane 1,1,1-triacetoxy-1,1-dihydro-1,2-benziodoxol-3(1H)-one
DIPEA N,N-diisopropylethylamine
DMF N,N-dimethylformamide
DMSO dimethylsulfoxide
EI electron impact ionization (MS)
eq. equivalent(s)
ESI electro-spray ionization (MS)
Et ethyl
EtOAc ethyl acetate
GC-MS gas chromatography-coupled mass spectroscopy
h hour(s)
Hal halogen
$^1$H-NMR proton nuclear magnetic resonance spectroscopy
HPLC high performance liquid chromatography
iPr isopropyl
LC-MS liquid chromatography-coupled mass spectroscopy
Me methyl
MeOH methanol
min minute(s)
MS mass spectroscopy
m/z mass-to-charge ratio (MS)
NBS N-bromosuccinimide
n-Bu n-butyl
NCS N-chlorosuccinimide
of th. of theory (chemical yield)
Pd/C palladium on charcoal
$PdCl_2$(dppf) [1,1'-bis(diphenylphosphino)ferrocene]dichloropalladium(II)
Pd(dba)$_2$ bis(dibenzylideneacetone)palladium
Ph phenyl
PPA polyphosphoric acid
q quartet ($^1$H-NMR signal)
quant. quantitative (yield)
rac racemic
$R_f$ TLC retention factor
RP reverse phase (HPLC)
rt room temperature
$R_t$ retention time (HPLC)
s singlet ($^1$H-NMR signal)
sat. saturated (solution)
t triplet ($^1$H-NMR signal)
TBAF tetra-n-butylammonium fluoride
TBDMS tert-butyldimethylsilyl
TBTU N-[(1H-benzotriazol-1-yloxy)(dimethylamino)methylene]-N-methylmethanaminium tetrafluoroborate
tBu tert-butyl
tert tertiary
TFA trifluoroacetic acid
THF tetrahydrofuran
TLC thin layer chromatography
LCMS (Method 1): HSST3
Instrument: Waters ACQUITY SQD UPLC system; column: Waters Acquity UPLC HSS T3 1.8 μm 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; flow rate: 0.40 ml/min; UV detection: 208-400 nm.

LCMS (Method 2): MHZ-QP-Gold

Instrument: Micromass Quattro Premier mit Waters UPLC Acquity system; column: Thermo Hypersil GOLD 1.9μ 50×1 mm; eluent A: 1 l water+0.5 ml 50% formic acid, eluent B: 1 l acetonitrile+0.5 ml 50% formic acid; gradient: 0.0 min 97% A→0.5 min 97% A→3.2 min 5% A→4.0 min 5% A oven: 50° C.; flow rate: 0.3 ml/min; UV detection: 210 nm.

LCMS (Method 3): MCW-FT-MS-M1

Instrument: Thermo Scientific FT-MS UHPLC+ system; Thermo Scientific UltiMate 3000; column: Waters, HSST3, 2.1×75 mm, C18 1.8 μm; eluent A: 1 l water+0.01% formic acid; eluent B: 1 l acetonitrile+0.01% formic acid; gradient: 0.0 min 10% B→2.5 min 95% B→3.5 min 95% B; oven: 50° C.; flow rate: 0.90 ml/min; UV detection: 210 nm/Optimum Integration Path 210-300 nm LCMS (Method 4): MCW SQ-HSST3 LONG Instrument: Waters ACQUITY SQD UPLC system; column: Waters Acquity UPLC HSS T3 1.8μ 50×1 mm; eluent A: 1 l water+0.25 ml 99% formic acid, eluent B: 1 l acetonitrile+0.25 ml 99% formic acid; gradient: 0.0 min 95% A→6.0 min 5% A→7.5 min 5% A oven: 50° C.; flow rate: 0.35 ml/min; UV detection: 210-400 nm.

GCMS (Method 1): DSQ-II

Instrument: Thermo Scientific DSQII, Thermo Scientific Trace GC Ultra system; column: Restek RTX-35MS, 15 m×200 μm×0.33 μm; constant helium flow: 1.20 ml/min; oven: 60° C.; inlet: 220° C.; gradient: 60° C., 30° C./min→300° C. (hold time 3.33 min).

HPLC Method 1:

System: High performance liquid chromatograph equipped with gradient pumps, UV detector & attached with data recorder and integrator software; column: Zorbax Eclipse XDB C18 (150 mm*3 mm, 3.5 μm); flow: 0.5 mL/min; column temperature: 30° C.; injection volume 10 μL, detection 226 nm, run time: 30 min; mobile phase A: 1.15 g $NH_4H_2PO_4$ and 1.16 g $H_3PO_4$ (85%) in 1 L milli-Q water; mobile phase B: acetonitrile; gradient:

| Time (min) | Mobile phase-A (% v/v) | Mobile phase-B (% v/v) |
|---|---|---|
| 0.0 | 95 | 5 |
| 5.0 | 40 | 60 |
| 15.0 | 30 | 70 |
| 25.0 | 20 | 80 |
| 25.1 | 95 | 5 |
| 30.0 | 95 | 5 |
| 30.01 | Stop | |

Example 1

3-(Methoxycarbonyl)-4-(3-thienyl)but-3-enecarboxylic Acid (XIII)

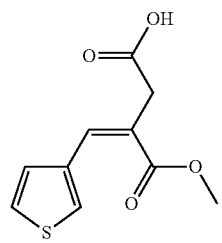

256 kg of dimethyl succinate are initially charged in 296 L of methanol. 332 kg of NaOMe (30% in MeOH) are added over a period of 2 h at a temperature from 25-40° C. The reaction mixture is heated to 65-70° C. and a solution of 98.5 kg of thiophene-3-aldehyde in 20 L of methanol is added over a period of 4 h. The mixture is further stirred for 2 h and subsequently cooled to 30-35° C. The solvent is distilled off under reduced pressure at <55° C. (residual volume ca. 400 L). The mixture is cooled to 10-30° C. and 296 L of toluene and 788 L of water are added. The phases are separated and the aqueous phase is adjusted between pH 1-3 with conc. HCl. The aqueous phase is extracted a further three times with a total of 789 L of toluene and the combined organic phases are washed with a solution of 98.5 kg of NaCl in 493 L of water. The solvent is distilled off under reduced pressure at <60° C. and 197 L of toluene are added to the residue at 35-40° C. The mixture is cooled to −5° C. and filtered. The filter residue is washed with 49 L of toluene and 197 L of hexane and then dried under reduced pressure at 45-50° C. 128.9 kg of 3 are obtained in 65% yield.

The crude product from laboratory experiments prepared analogously to the above procedure—but on a smaller scale—was additionally purified according to the following method for analytical characterization:

45 g of crude product in 90 mL of toluene were stirred at 40° C. for 1 h and subsequently cooled to −5° C. over a period of 2 h and isolated on a filter. The filter residue was further washed with cold toluene and hexane and dried in a vacuum drying cabinet at 40° C. 25.6 g of (XIII) were obtained and characterized:

$^1$H NMR (600 MHz, DMSO-$d_6$) δ ppm 3.53 (s, 2H), 3.74 (s, 3H), 7.31 (dd, J=4.95, 1.10 Hz, 1H), 7.67 (dd, J=4.95, 2.93 Hz, 1H), 7.75 (s, 1H), 7.86 (d, J=2.57 Hz, 1H), 12.53 (br s, 1H)

LCMS (method 3): $R_t$=1.27 min; MS (ESIpos): m/z=227 $(M+H)^+$

Example 2

Methyl 7-acetoxy-1-benzothiophene-5-carboxylate (XII)

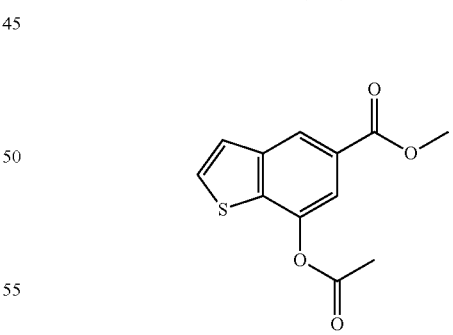

73.1 kg of (XIII) are initially charged in 731 L of toluene and 115.5 kg of acetic anhydride and 32.2 kg of sodium acetate are added. The reaction mixture is heated to 70-75° C. for 7 h. 366 L of water are added at 25-30° C. and the phases separated and the organic phase is washed with 366 L of water. The organic phase is concentrated under reduced pressure at <60° C. up until a residual volume of 300-360 L remains. The crude product is used as a solution in the next stage.

The analytical characterization was carried out on a sample from the following laboratory procedure:

204 g of intermediate (XIII) are initially charged in 720 mL of toluene and 230 g of acetic anhydride and 89 g of sodium acetate are added. The reaction mixture is heated to 70-75° C. for 7 h. After cooling, the reaction mixture is filtered, the filtrate is washed with 1 L of water and the phases are separated. The organic phase is washed with 1 L of sat. aqueous NaCl solution. The organic phase is concentrated under reduced pressure at <60° C., and 2×200 mL of ethanol are added and the mixture again concentrated. 202 g of crude product 4 are obtained, and may be used without further purification in the next stage.

10 g of the crude product are recrystallised from 50 mL of diisopropyl ether and dried in the drying cabinet at 40° C.

$^1$H NMR (400 MHz, DMSO-$d_6$) δ ppm 2.41 (s, 3H), 3.91 (s, 3H), 7.70 (d, J=5.38 Hz, 1H), 7.76 (s, 1H), 7.95 (d, J=5.38 Hz, 1H), 8.46 (s, 1H)

LCMS (method 4): $R_t$=2.72 min; MS (ESIpos): m/z=251 (M+H)$^+$

Example 3

7-Hydroxy-1-benzothiophene-5-carboxylic acid (XI)

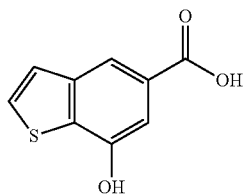 [SMILES: O=C(O)c1cc(O)c2sccc2c1]

146 L of methanol and 292 L of water are added to the concentrated crude solution of (XII) at 25-30° C. and a solution of 77.5 kg of NaOH in 366 L of water are added at <45° C. over a period of 1.5 h. The reaction mixture is heated to 50-55° C. for 5 h. The phases are separated and the aqueous phase is further diluted with 73 L of water. The aqueous phase is acidified to pH 2-3 with semi-concentrated sulphuric acid at 10-15° C. and then heated to 40-45° C. for a further 1 h. After slow cooling to 25-30° C. over a period of 2 h, the product is isolated on a centrifugal filter and washed with 219 L of water. After drying in the warm air dryer at 60-65° C., 57.5 kg of intermediate (XI) were obtained (yield: 92%).

The analytical characterization was carried out on a sample from the following laboratory procedure:

2.0 g of 4 were initially charged in 15 mL of ethanol and 5 mL of THF at room temperature and 20 mL of aqueous sodium hydroxide solution (2 molar) were added. The mixture is heated to 50° C. for 3 h and then 50 mL of ethyl acetate and 10 mL of toluene are added. The phases are separated and the aqueous phase is acidified with 3.6 g of semi-concentrated sulphuric acid. The suspension is cooled to 0° C. and filtered. The filter residue is washed with water and dried in the vacuum drying cabinet at 40° C. 1.4 g (90%) of (XI) are obtained and characterized:

$^1$H NMR (400 MHz, DMSO-$d_6$) δ ppm 2.50 (dt, J=3.55, 1.77 Hz, 1H), 2.54 (s, 1H) 3.32 (s, 3H), 7.33 (d, J=1.10 Hz, 1H), 7.53 (d, J=5.38 Hz, 1H), 7.79 (d, J=5.38 Hz, 1H), 8.00 (d, J=1.34 Hz, 1H), 10.64 (s, 1H), 12.79 (s, 1H)

LCMS (method 1): $R_t$=0.67 min; MS (ESI neg): m/z=194 (M–H)

Example 4

Methyl 7-methoxy-1-benzothiophene-5-carboxylate (X)

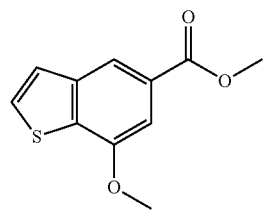

Method A:

61.0 kg of intermediate (XI) are initially charged in 244 L of acetone and 427 L of toluene and 130.2 kg of $K_2CO_3$ are added. The suspension is heated to 50-60° C. and 79.2 kg of dimethyl sulphate are added over a period of 1 h. The mixture is stirred for a further 8 h at this temperature and the solvent is subsequently distilled off at 85° C. until no further distillate passes over.

After cooling to 25-30° C., 610 L of water are added and the phases are separated. The aqueous phase is extracted with 244 L of toluene, the combined organic phases are washed with 305 L of water and the solvent is distilled off under reduced pressure at 60° C. The crude product (X) is used without further purification in the next stage.

Method B:

18.5 g of intermediate (XV) are initially charged in 220 mL of 2-butanone and 18.4 g of potassium carbonate are added and the mixture stirred at room temperature for 5 minutes. 8.4 mL of dimethyl sulphate are then added and the mixture is stirred at room temperature for 5 h. To the suspension are added 26.7 mL of 28% ammonia solution, 220 mL of water and 220 mL of methyl t-butyl ether and the mixture is stirred for 1 h. The phases are separated and the aqueous phase is extracted with 3×220 mL of methyl t-butyl ether. The combined organic phases are dried over sodium sulphate and concentrated under reduced pressure at 40° C. Intermediate (X) is obtained in quantitative yield.

For analytical characterization a combined sample from several laboratory experiments was purified by preparative chromatography and characterized:

11.4 g of crude product (X) were purified chromatographically on ca. 370 g of silica gel using n-heptane and ethyl acetate (95:5 to 90:10). 7.4 g of 6 were obtained by concentrating the main fraction and characterized analytically:

$^1$H NMR (400 MHz, DMSO-$d_6$) δ ppm 3.91 (s, 3H), 4.03 (s, 3H), 7.40 (s, 1H), 7.61 (d, J=5.26 Hz, 1H), 7.88 (d, J=5.38 Hz, 1H), 8.19 (s, 1H)

GCMS (method 1): Rt=6.51 min; MS: m/z=222 (M)$^+$

Example 5

(7-methoxy-1-benzothiophen-5-yl)methanol (IX)

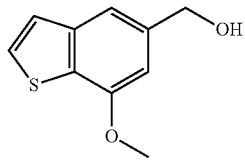

The crude product (X) from the preceding stage is dissolved in 244 L of THF and 159 kg of a 60% solution of sodium bis(2-methoxyethoxy)aluminium dihydride (Red-Al®) in toluene is added at 25-30° C. over a period of 3 h. The reaction mixture is stirred for a further 3 h, cooled to 0-5° C. and subsequently hydrolysed with a solution of 61.0 kg of NaOH in 610 L of water at <25° C. 122 L of toluene is then added at 25-30° C., the phases are separated and the aqueous phase is extracted with 305 L of toluene. The combined organic phases are washed with a solution of 61 kg of NaCl in 305 L of water and concentrated under reduced pressure at 60° C. Intermediate (IX) is used without further purification in the following stage.

A sample for analytical characterisation was prepared according to the following procedure:

26.3 g of (X) are dissolved in 230 mL of THF and 25.2 mL of a 2.4 molar solution of lithium aluminium hydride in THF are added at 10-20° C. over a period of 10 min. The reaction mixture is stirred for a further 1 h and subsequently hydrolysed with 84 mL of aqueous hydrochloric acid (1M) in an ice bath.

130 mL of methyl tert-butyl ether are added and adjusted to pH 1 with 80 mL of aqueous hydrochloric acid (2M). The aqueous phase is separated and extracted with methyl tert-butyl ether. The combined organic phases are washed with 50 mL of 5% aqueous saline solution, dried over Na$_2$SO$_4$ and concentrated under reduced pressure. The residue is purified by preparative chromatography on 900 g of silica gel (eluent n-heptane: ethyl acetate 70:30 to 65:35). 18.5 g (92%) of product (IX) are obtained as an oil.

$^1$H NMR (400 MHz, DMSO-$d_6$) δ ppm 3.95 (s, 3H), 4.61 (d, J=5.75 Hz, 2H), 5.25 (t, J=5.75 Hz, 1H), 6.90 (s, 1H), 7.37-7.45 (m, 2H) 7.70 (d, J=5.26 Hz, 1H)

GCMS (method 1): R$_t$=6.45 min; MS: m/z=194 (M)$^+$

Example 6

5-(Chloromethyl)-1-benzothiophen-7-yl methyl ether (VIII)

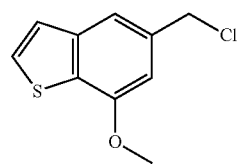

Intermediate (IX) is heated to 50-55° C. in 852 L of toluene and 609 L of concentrated aqueous HCl are added over a period of 90 min. The mixture is stirred for a further 6 h and then cooled to 25-30° C. The phases are separated and the organic phase is added to a solution of 54.8 kg of NaHCO$_3$ in 609 L of water. The organic phase is separated, washed with 61 kg of NaCl in 304 L of water and 60.9 kg of Na$_2$SO$_4$ are added. The suspension is filtered and the filter cake is washed with 61 L of toluene. The solvent is distilled off under reduced pressure at <60° C. and (VIII) is used without further purification in the next stage.

A sample for analytical characterization was produced according to the following procedure:

6.3 ml of thionyl chloride were added to 14.0 g of intermediate (IX) in 210 mL of toluene at room temperature and the mixture is stirred for 2 h. The reaction mixture is concentrated under reduced pressure at 60° C. and toluene is added twice more, 150 ml each time, and the mixture concentrated.

The residue is taken up in 230 mL of methyl tert-butyl ether and 150 mL of water. 30 mL of 10% aqueous saline solution are added and the mixture neutralized with 15 mL of saturated aqueous NaHCO$_3$ solution. The organic phase is washed with 30 mL of 10% aqueous saline solution and concentrated under reduced pressure. For drying, the residue is treated twice with a little ethyl acetate and concentrated. 14.20 g (93%) of product (VIII) are obtained as an oil.

GCMS (method 1): Rt=6.29 min; MS: m/z=212 (M)$^+$

Example 7

7-Methoxy-5-methyl-1-benzothiophene (VII)

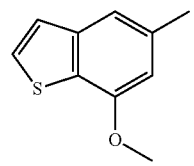

The crude product (VIII) from the preceding stage is dissolved in 304 L of THF and 237.5 kg of a 60% solution of sodium bis(2-methoxyethoxy)aluminium dihydride (Red-Al®) in toluene are added at 20-35° C. over a period of 4 h. The reaction mixture is stirred for a further 2 h, cooled to 0-5° C. and subsequently a solution of 91.3 kg of NaOH in 913 L of water is added slowly at <25° C. 122 L of toluene are then added at 25-30° C., the phases separated and the aqueous phase extracted with 304 L of toluene. The combined organic phases are washed with a solution of 60.9 kg of NaCl in 305 L of water and concentrated under reduced pressure at 60° C. The crude product is purified by fractional distillation at 125-160° C. under high vacuum. 34.3 kg of intermediate (VII) were obtained.

HPLC (method 1): area %: 99.56% VII; content: 99.9% by weight

Example 8

(7-Methoxy-5-methyl-1-benzothiophen-2-yl)boronic acid (VI)

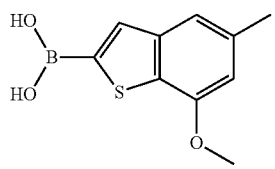

357 L of THF are cooled to −68 to −80° C. and 118.2 kg of n-butyllithium (2.5M in hexane) are added at this temperature. The mixture is subsequently further cooled to −73 to −80° C.

In a further reaction vessel, 51.0 kg of (VII) are dissolved in 87 L of THF and are added slowly to the highly cooled n-butyllithium solution previously prepared. The reaction mixture is then stirred a further 30 minutes at the lower temperature and 109 L of triisopropyl borate are then added at −70 to −80° C. After 30 min, 20.9 kg of KOH in 102 L of water are added at <10° C. The mixture is then further diluted with 663 L of water and the organic phase separated at 20-30° C.

The aqueous phase is washed 3 times with 153 L of toluene, cooled to 0 to 5° C. and slowly acidified to pH 2-3 with semi-concentrated sulphuric acid. After 3 h at 0 to −5° C., the mixture is filtered and the filter residue washed with 510 L of water. The moist filter cake is suspended in 510 L of cyclohexane at 40-45° C., isolated by filtration at 20-35° C. and washed on the filter with 255 L of cyclohexane.

The product is dried in the vacuum drying cabinet at 40-45° C. 64.8 kg of (VI) are obtained having a water content of ca. 10% to 15%.

HPLC (method 1) area %: 99.01% VI, 0.97% VII; content: 88.6% by weight

A sample for NMR characterization was produced following the identical procedure as described above, but on smaller laboratory scale:

$^1$H NMR (500 MHz, DMSO-d$_6$) δ ppm 2.43 (s, 3H), 3.93 (s, 3H), 6.77 (s, 1H), 7.29 (s, 1H), 7.86 (s, 1H), 8.44 (s, 2H)

Alternative Synthetic Intermediates

Example 9

Methyl 7-hydroxy-1-benzothiophene-5-carboxylate (XV)

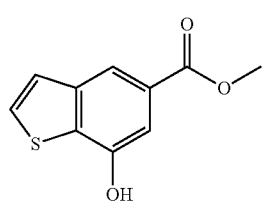

22.6 g of intermediate (X) are initially charged in 560 mL of ethanol and 13.7 g of K$_2$CO$_3$ are added. The suspension is heated to reflux for 4 h and subsequently concentrated under reduced pressure at 40° C.

560 mL of water and 560 mL of methyl t-butyl ether are added to the residue and the pH is adjusted to 2-3 with 2M aqueous HCl. The phases are separated and the aqueous phase is extracted with 3×230 mL of methyl t-butyl ether. The combined organic phases are dried over sodium sulphate and concentrated under reduced pressure at 40° C. 18.8 g of intermediate (XV) are obtained in quantitative yield.

$^1$H NMR (400 MHz, DMSO-d$_6$) δ ppm 3.87 (s, 3H), 7.34 (d, J=0.98 Hz, 1H), 7.55 (d, J=5.26 Hz, 1H), 7.82 (d, J=5.38 Hz, 1H), 8.03 (d, J=1.10 Hz, 1H), 10.73 (s, 1H)

LCMS (method 3): R$_t$=1.52 min; MS (ESI pos): m/z=209 (M+H)$^+$

Example 10

5-(Hydroxymethyl)-1-benzothiophen-7-ol (XVI)

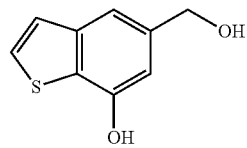 [SMILES: OCc1cc(O)c2sccc2c1]

25.0 g of intermediate (XI) are initially charged in 250 mL of tetrahydrofuran and 117.1 g of a 60% solution of sodium bis(2-methoxyethoxy)aluminium dihydride (Red-Al®) in toluene are added at 15-20° C. over a period of 1.5 h. The reaction mixture is stirred for a further 20 h, cooled to 5-10° C. and subsequently 300 mL of 2M aqueous hydrochloric acid and 100 mL of water are added slowly. 350 mL of methyl t-butyl ether are added and the mixture is filtered over diatomaceous earth with a further 100 mL of methyl t-butyl ether. The phases are separated and the aqueous phase is extracted with 2×60 mL of methyl t-butyl ether. The combined organic phases are washed with 50 mL of water, dried over Na$_2$SO$_4$ and concentrated under reduced pressure at 35° C. 18.4 g of intermediate (XVI) are obtained.

$^1$H NMR (400 MHz, DMSO-d$_6$) δ ppm 4.53 (d, J=5.75 Hz, 2H), 5.16 (t, J=5.75 Hz, 1H), 6.76 (s, 1H), 7.27 (s, 1H), 7.35 (d, J=5.26 Hz, 1H), 7.64 (d, J=5.26 Hz, 1H), 10.19 (s, 1H) LCMS (method 1): Rt=0.58 min; MS (ESI pos): m/z=179 (M−H)$^−$

We claim:

1. A method of preparing a compound of formula (VI):

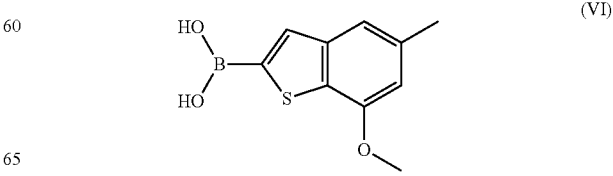

comprising
dissolving a compound of formula (VII):

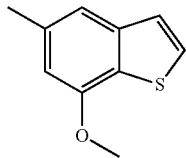
(VII)

in an inert solvent, and adding a metal organic base and a trialkyl borate,
thereby providing a compound of formula (VI):

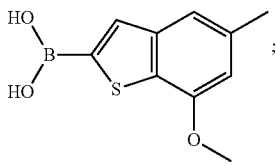
(VI)

wherein the method comprises preparing said compound of formula (VII):

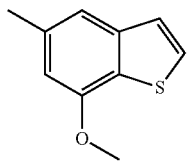
(VII)

by reacting a compound of formula (X):

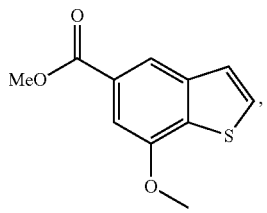
(X)

with one or more reducing agents, thereby providing a compound of formula (IX):

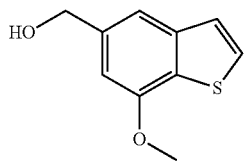
(IX)

and reacting the compound of formula (IX) with aqueous HCl in the presence of a solvent, thereby providing a compound of formula (VIII):

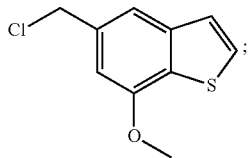
(VIII)

and reacting the compound of formula (VIII) with one or more reducing agents, thereby providing a compound of formula (VII).

2. The method according to claim 1, comprising preparing said compound of formula (X):

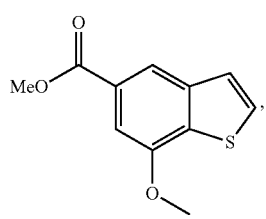
(X)

by reacting a compound of formula (XI):

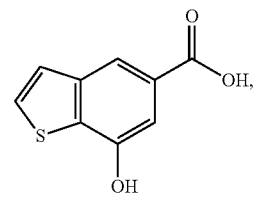
(XI)

in the presence of a methylating agent, in a solvent, thereby providing a compound of formula (X).

3. The method according to claim 2, comprising preparing said compound of formula (XI):

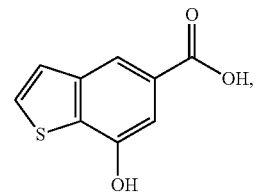
(XI)

by reacting a compound of formula (XII):

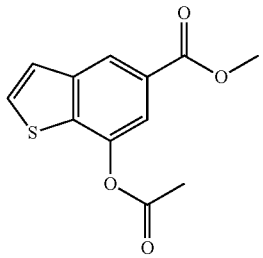
(XII)

in the presence of a base and treating with a strong protic acid, thereby providing a compound of formula (XI).

4. The method according to claim 1, comprising preparing said compound of formula (X):

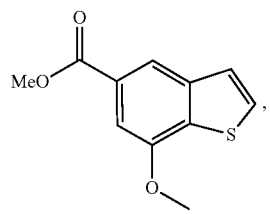
(X)

by reacting a compound of formula (XII):

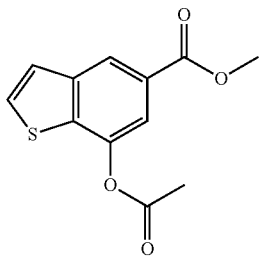
(XII)

with a base in the presence of a solvent, thereby providing a compound of formula (XV):

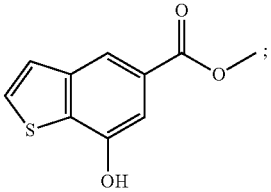
(XV)

and subsequently reacting the compound of formula (XV) in the presence of a methylating agent, thereby providing the compound of formula (X).

5. The method according to claim 3, comprising preparing the compound of formula (XII):

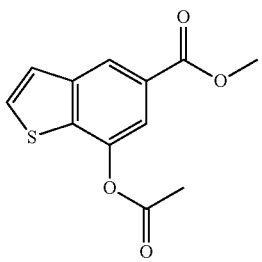
(XII)

by reacting a compound of formula (XIII):

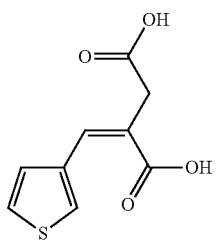
(XIII)

with a dehydrating agent in the presence of a base and hydrolyzing the reaction product by adding water, thereby providing the compound of formula (XII).

6. The method according to claim 5, comprising preparing the compound of formula (XIII):

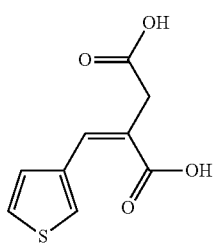
(XIII)

by reacting a compound of formula (XV):

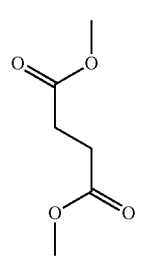
(XV)

with a compound of formula (XIV):

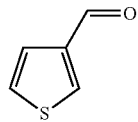
(XIV)

in the presence of a base in a solvent thereby providing the compound of formula (XIII).

7. The method according to claim 4, comprising preparing the compound of formula (XII):

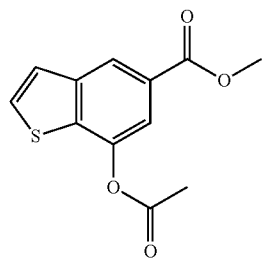
(XII)

by reacting a compound of formula (XIII):

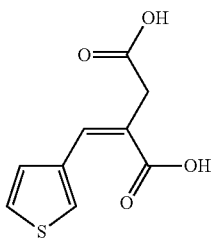
(XIII)

with a dehydrating agent in the presence of a base and hydrolyzing the reaction product by adding water, thereby providing the compound of formula (XII).

8. The method according to claim 7, comprising preparing the compound of formula (XIII):

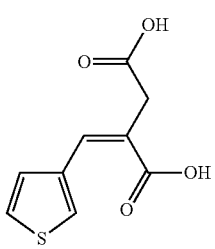
(XIII)

by reacting a compound of formula (XV):

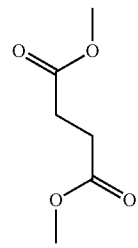
(XV)

with a compound of formula (XIV):

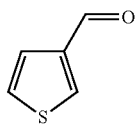
(XIV)

in the presence of a base in a solvent thereby providing the compound of formula (XIII).

9. The method of claim 1, comprising dissolving the compound of formula (VII) in THF.

10. The method of claim 1, wherein the metal organic base is a n-butyl lithium solution.

11. The method of claim 1, wherein the trialkyl borate is triisopropyl borate.

12. The method of claim 1, wherein the metal organic base and trialkyl borate are in a solvent.

13. The method of claim 12, wherein the metal organic base and trialkyl borate are in THF.

14. The method of claim 1, comprising reacting the compound of formula (X) with one or more reducing agents in the presence of an inert solvent.

15. The method of claim 14, comprising reacting the compound of formula (X) with one or more reducing agents in the presence of THF.

16. The method of claim 1, comprising reacting the compound of formula (X) with sodium-bis(2-methoxy-ethoxy)-aluminium-dihydride solution.

17. The method of claim 1, comprising reacting the compound of formula (IX) with aqueous HCl in the presence of toluene.

18. The method of claim 1, comprising reacting the compound of formula (VIII) with sodium-bis(2-methoxy-ethoxy)-aluminium-dihydride solution.

19. The method of claim 2, comprising reacting the compound of formula (XI) with dimethylsulfate.

20. The method of claim 2, comprising reacting the compound of formula (XI) with the methylating agent in a mixture of acetone and toluene.

21. The method of claim 3, comprising reacting the compound of formula (XII) in the presence of an aqueous sodium hydroxide solution.

22. The method of claim 3, comprising reacting the compound of formula (XII) in the presence of the base and treating with $H_2SO_4$.

23. The method of claim 4, comprising reacting the compound of formula (XII) with potassium carbonate.

24. The method of claim 4, comprising reacting the compound of formula (XII) with the base in the presence of ethanol.

25. The method of claim 4, comprising reacting the compound of formula (XV) in the presence of dimethylsulfate.

26. The method of claim 4, comprising reacting the compound of formula (XV) in the presence of the methylating agent in the presence of a base.

27. The method of claim 5, comprising reacting the compound of formula (XIII) with acetic anhydride.

28. The method of claim 5, comprising reacting the compound of formula (XIII) with the dehydrating agent the presence of sodium acetate.

29. The method of claim 6, comprising reacting the compound of formula (XV) with the compound of formula (XIV) in the presence of sodium methanolate.

30. The method of claim 6, comprising reacting the compound of formula (XV) with the compound of formula (XIV) in methanol.

31. The method of claim 7, comprising reacting the compound of formula (XIII) with acetic anhydride.

32. The method of claim 7, comprising reacting the compound of formula (XIII) with the dehydrating agent the presence of a sodium acetate.

33. The method of claim 8, comprising reacting the compound of formula (XV) with the compound of formula (XIV) in the presence of sodium methanolate.

34. The method of claim 8, comprising reacting the compound of formula (XV) with the compound of formula (XIV) in methanol.

\* \* \* \* \*